US012127981B2

(12) United States Patent
Durham

(10) Patent No.: US 12,127,981 B2
(45) Date of Patent: *Oct. 29, 2024

(54) EYEWEAR FRAME WITH INTEGRAL ROLL-OFF SYSTEM

(71) Applicant: Fox Head, Inc., Irvine, CA (US)

(72) Inventor: David Leroy Durham, San Clemente, CA (US)

(73) Assignee: Fox Head, Inc., Irvine, CA (US)

( * ) Notice: Subject to any disclaimer, the term of this patent is extended or adjusted under 35 U.S.C. 154(b) by 101 days.

This patent is subject to a terminal disclaimer.

(21) Appl. No.: 17/974,332

(22) Filed: Oct. 26, 2022

(65) Prior Publication Data
US 2023/0129030 A1    Apr. 27, 2023

Related U.S. Application Data

(63) Continuation of application No. 16/714,519, filed on Dec. 13, 2019, now Pat. No. 11,510,816.

(51) Int. Cl.
*A61F 9/02* (2006.01)
(52) U.S. Cl.
CPC .............. *A61F 9/029* (2013.01); *A61F 9/025* (2013.01)
(58) Field of Classification Search
CPC ................................ A61F 9/025; A61F 9/029
USPC .......................................................... 2/438
See application file for complete search history.

(56) References Cited

U.S. PATENT DOCUMENTS

| 5,809,580 | A * | 9/1998 | Arnette ................... A61F 9/027 2/426 |
| 6,388,813 | B1 | 5/2002 | Wilson et al. |
| 6,536,045 | B1 | 3/2003 | Wilson et al. |
| 6,725,467 | B2 * | 4/2004 | Harding .................. A61F 9/025 2/435 |
| 6,847,492 | B2 | 1/2005 | Wilson et al. |

(Continued)

FOREIGN PATENT DOCUMENTS

| EP | 2564820 A1 | 3/2013 |
| GB | 2378412 A | 2/2003 |

(Continued)

OTHER PUBLICATIONS

International Searching Authority, International Search Report and Written Opinion, PCT Patent Application PCT/US2022/019406, mailed Jun. 7, 2022, 15 pages.

*Primary Examiner* — F Griffin Hall
(74) *Attorney, Agent, or Firm* — Reed Smith LLP; Walter M. Egbert, III; Richard J. Brown

(57) ABSTRACT

A goggle includes a frame, a lens, and a roll-off system. The frame has a first lateral end and an opposing second lateral end. The frame defines a lens cavity. The lens is disposed within the lens cavity of the frame. The roll-off system includes a first canister, a second canister, and an actuator mechanism. The first canister is at least partially integrally formed with the first lateral end of the frame. The first canister defines a first interior cavity configured to store a roll of film. The second canister is at least partially integrally formed with the opposing second lateral end of the frame. The second canister defines a second interior cavity configured to receive a strip of film from the roll of film. The actuator mechanism is configured to facilitate selectively dispensing the strip of film from the first canister across the lens to the second canister.

32 Claims, 5 Drawing Sheets

(56) References Cited

U.S. PATENT DOCUMENTS

| | | |
|---|---|---|
| 7,184,217 B2 | 2/2007 | Wilson et al. |
| 9,295,297 B2 | 3/2016 | Wilson |
| D755,278 S | 5/2016 | Blanchard et al. |
| 9,526,290 B2 | 12/2016 | Wilson |
| 9,839,558 B2 | 12/2017 | Blanchard et al. |
| 9,918,876 B2 | 3/2018 | Wilson et al. |
| 9,968,155 B2 | 5/2018 | Wilson |
| 10,070,678 B2 | 9/2018 | Wilson |
| 10,226,095 B2 | 3/2019 | Wilson |
| 10,321,731 B2 | 6/2019 | Wilson |
| 10,357,400 B2 | 7/2019 | Ginther et al. |
| 11,173,068 B2 | 11/2021 | Wilson et al. |
| 2014/0157496 A1 * | 6/2014 | Ginther .................. A61F 9/029 2/439 |
| 2017/0354540 A1 * | 12/2017 | Yang ....................... B08B 1/006 |
| 2021/0177659 A1 | 6/2021 | Durham |
| 2021/0393440 A1 | 12/2021 | Leatt et al. |
| 2022/0071335 A1 | 3/2022 | Wilson |
| 2022/0291529 A1 | 9/2022 | Munn et al. |

FOREIGN PATENT DOCUMENTS

| | | | |
|---|---|---|---|
| GB | 2371877 B | 4/2003 | |
| GB | 2376753 B | 1/2004 | |
| WO | 2007083900 A1 | 7/2007 | |
| WO | WO-2017189130 A1 * | 11/2017 | ............. A61F 9/025 |
| WO | 2019169345 A2 | 9/2019 | |
| WO | 2022192301 A1 | 9/2022 | |

* cited by examiner

EYEWEAR FRAME WITH INTEGRAL ROLL-OFF SYSTEM

CROSS-REFERENCE TO RELATED APPLICATIONS

This application is a continuation of U.S. patent application Ser. No. 16/714,519, filed Dec. 13, 2019, and titled EYEWEAR FRAME WITH INTEGRAL ROLL-OFF SYSTEM, which is incorporated herein in its entirety by reference thereto.

BACKGROUND

Eyewear, such as goggles, are typically worn to protect the wearer's eyes from radiation and foreign objects. In active sports, particularly, the lens of the eyewear may become dirty or collect dust, snow or other type of debris that block the view of the wearer. It would be desirable to implement a lens cleaning mechanism that can be deployed to quickly and efficiently remove debris from the lens and provide the wearer with an unobstructed view.

SUMMARY

One embodiment relates to a goggle. The goggle includes a frame, a lens, and a roll-off system. The frame may have a first lateral end and an opposing second lateral end. The frame may define a lens cavity. The lens may be disposed within the lens cavity of the frame. The roll-off system may include a first canister, a second canister, and an actuator mechanism. The first canister may be at least partially integrally formed with the first lateral end of the frame. The first canister may define a first interior cavity configured to store a roll of film. The second canister may at least partially integrally formed with the opposing second lateral end of the frame. The second canister may define a second interior cavity configured to receive a strip of film from the roll of film. The actuator mechanism may facilitate selectively dispensing the strip of film from the first canister across the lens to the second canister.

In some embodiments, the first lateral end of the frame defines a first slot and a first channel extending from the first slot through the first lateral end of the frame to the first interior cavity of the first canister.

In some embodiments, the opposing second lateral end of the frame defines a second slot and a second channel extending from the second slot through the opposing second lateral end of the frame to the second interior cavity of the second canister.

In some embodiments, the first canister and the second canister extend from a rear side of the frame. In some embodiments, the first canister and the second canister extend from a front side of the frame.

In some embodiments, the first canister includes a first housing and a first cap. The first housing may be integrally formed with the frame. The first cap may be detachably coupled to the first housing to facilitate selectively accessing and enclosing the first interior cavity of the first canister. In some embodiments, the second canister includes a second housing and a second cap. The second housing may be integrally formed with the frame. The second cap may be detachably coupled to the second housing to facilitate selectively accessing and enclosing the second interior cavity of the second canister.

In some embodiments, the actuator mechanism includes a pull-cord configured to facilitate manually dispensing the strip of film between the first canister and the second canister.

In some embodiments, the first lateral end of the frame defines a first rip-off interface. The opposing second lateral end of the frame may define a second rip-off interface. A first lateral end of the lens may define a third rip-off interface. An opposing second lateral end of the lens may define a fourth rip-off interface. In some embodiments, at least one of the first rip-off interface and the third rip-off interface. In some embodiments, at least one of the second rip-off interface and the fourth rip-off interface facilitate detachably coupling a rip-off film sheet across the lens. In some embodiments, the at least two of the first rip-off interface, the second rip-off interface, the third rip-off interface, and the fourth rip-off interface define an extension and/or define an aperture configured to detachably receive the extension.

In some embodiments, the lens is removable.

Another embodiment relates to a frame for a goggle. The frame includes a frame body, a first canister, and a second canister. The frame body has a first lateral end and an opposing second lateral end. The first canister is at least partially integrally formed with the first lateral end of the frame body. The first canister defines a first interior cavity configured to store a roll of film. The second canister is at least partially integrally formed with the opposing second lateral end of the frame body. The second canister defines a second interior cavity configured to receive a strip of film from the roll of film.

In some embodiments, the first canister includes a first housing integrally formed with the frame body and a first cap detachably coupled to the first housing to facilitate selectively accessing and enclosing the first interior cavity of the first canister. In some embodiments, the first housing of the first canister extends from a rear side of the frame body. In some embodiments, the first lateral end defines a first slot and a first channel extending from the first slot through the first lateral end to the first interior cavity of the first canister.

In some embodiments, the second canister includes a second housing integrally formed with the frame body and a second cap detachably coupled to the second housing to facilitate selectively accessing and enclosing the second interior cavity of the second canister. In some embodiments, the second housing of the second canister extends from the rear side of the frame body. In some embodiments, the opposing second lateral end defines a second slot and a second channel extending from the second slot through the opposing second lateral end to the second interior cavity of the second canister.

In some embodiments, the first lateral end of the frame body defines a first rip-off interface and the opposing second lateral end of the frame body defines a second rip-off interface. In some embodiments, the first rip-off interface and the second rip-off interface facilitate detachably coupling a rip-off film sheet across a lens received within the frame.

In some embodiments, the first rip-off interface and the second rip-off interface define an extension and/or define an aperture configured to detachably receive the extension.

Still another embodiment relates to an eyewear. The eyewear includes a frame, a lens, a first canister, and a second canister. The frame has a first lateral end defining a first channel, an opposing second lateral end defining a second channel, a front side, and an opposing rear side. The lens is disposed within the frame. The first canister is coupled to the first lateral end of the frame. The first canister includes a first housing and a first cap. The first housing is integrally formed with and extends from the opposing rear side of the frame. The first cap is detachably coupled to the first housing. The first housing and the first cap cooperatively define a first interior cavity of the first canister. The second canister is coupled to the opposing second lateral end of the frame. The second canister includes a second housing and a second cap. The second housing is integrally formed with and extends from the opposing rear side of the frame. The second cap is detachably coupled to the second housing. The second housing and the second cap cooperatively define a second interior cavity of the second canister. The first channel extends from the front side of the frame through the first lateral end of the frame to the first interior cavity of the first canister. The second channel extends from the front side of the frame through the opposing second lateral end of the frame to the second interior cavity of the second canister.

In some embodiments, a method is provided. The method may include providing a frame. The frame may include a frame body, a first canister, and a second canister. The frame body may have a first lateral end and an opposing second lateral end. The first canister may at least partially be integrally formed with the first lateral end of the frame body. The first canister may define a first interior cavity configured to store a roll of film. The second canister may at least partially be integrally formed with the opposing second lateral end of the frame body. The second canister may define a second interior cavity configured to receive a strip of film from the roll of film. The method may also include coupling a lens to the frame.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The drawings are provided to illustrate example embodiments described herein and are not intended to limit the scope of the disclosure. Throughout the drawings, reference numbers may be re-used to indicate general correspondence between referenced elements.

DETAILED DESCRIPTION

Figure 1:
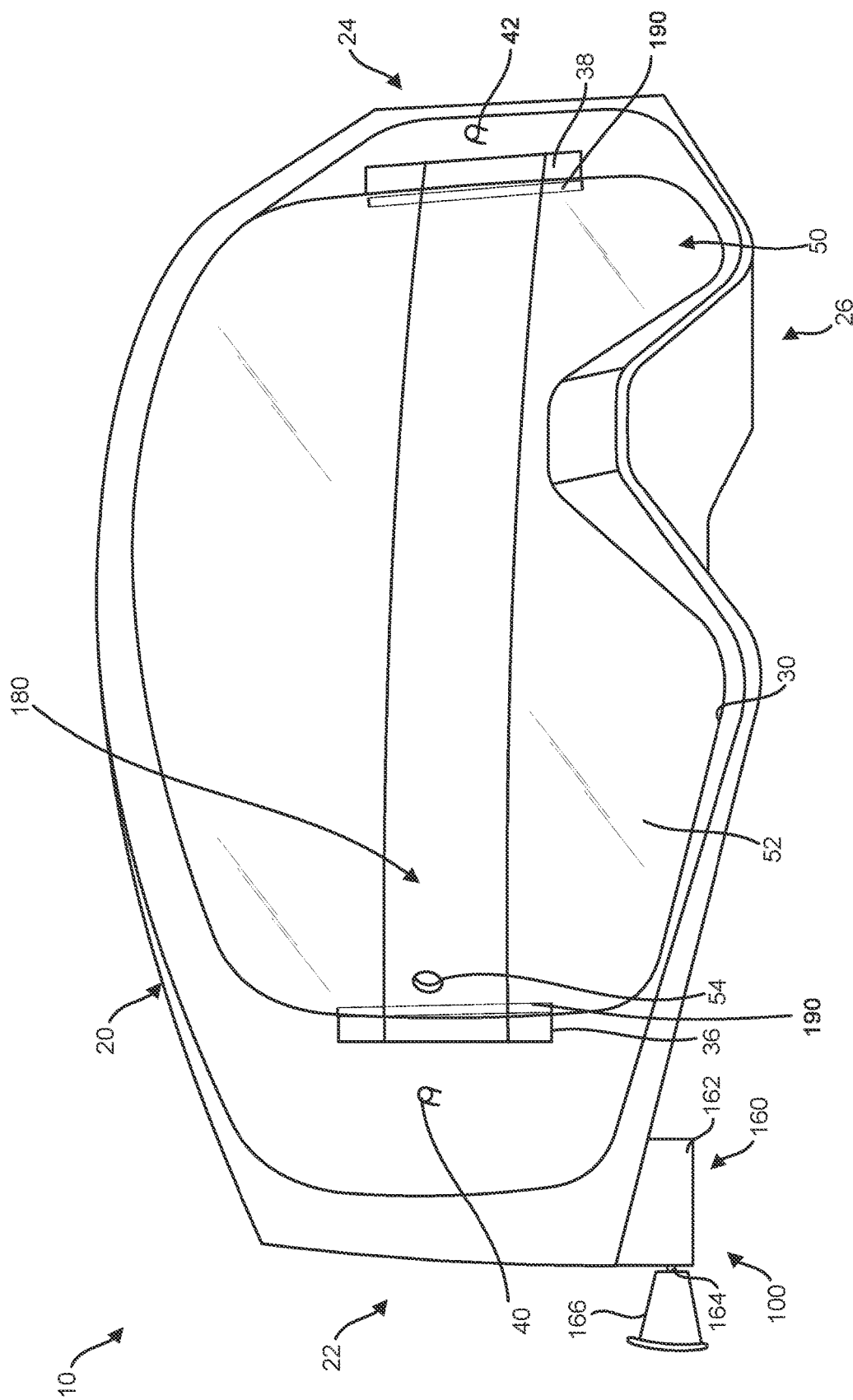
FIG. 1 is a front perspective view of eyewear having a roll-off system, according to an example embodiment.

Various aspects of the disclosure will now be described with regard to certain examples and embodiments, which are intended to illustrate but not to limit the disclosure. Nothing in this disclosure is intended to imply that any particular feature or characteristic of the disclosed embodiments is essential. The scope of protection is defined by the claims that follow this description and not by any particular embodiment described herein. Before turning to the figures, which illustrate example embodiments in detail, it should be understood that the application is not limited to the details or methodology set forth in the description or illustrated in the figures. It should also be understood that the terminology is for the purpose of description only and should not be regarded as limiting.

Embodiments herein generally relate to a lens cleaning system (e.g., an integral roll-off system, etc.). The lens cleaning system may facilitate cleaning a lens of eyewear, which may include goggles, glasses, sunglasses, protective eyewear, and the like. For example, the lens cleaning system may be configured to facilitate selectively cleaning the lens in a relatively simple manner (e.g., easily, quickly, etc.), by removing debris that hinder the vision of the wearer from the lens, and the like.

The eyewear described herein having the lens cleaning system may be used in a number of activities, including sports and athletics, such as extreme sports (e.g., motocross and snowmobiling); cycling activities, including auto racing, motorcycle riding and racing, BMX, mountain biking, etc.; with recreational vehicles including all-terrain vehicles (ATVs), dirt bikes, utility task vehicles (UTVs), snowmobiles, and other off-road vehicles; military applications; and/or construction applications. For example, in some embodiments, the eyewear is a motocross goggle. In other embodiments, the eyewear is a snowmobiling goggle, a snowboarding goggle, a mountain biking goggle, a motorcycle goggle, a sky diving goggle, or still another action or extreme sport goggle. In still other embodiments, the eyewear is or includes a swimming goggle or other sports goggle (e.g., used in basketball, baseball, etc.; Rec Specs®; etc.). In another embodiment, the eyewear is or includes a visor coupled to a helmet (e.g., a football helmet, a motorcycle helmet, etc.). In yet other embodiments, the eyewear is another type of eyewear used for construction, military applications, machining, carpentry, scientific experimentation, and/or the like. In still other embodiments, the eyewear is a traditional vision enhancing glasses (e.g., prescription glasses, etc.) and/or sunglasses.

In some embodiments, the eyewear of the present disclosure includes a frame, a lens (e.g., a permanently attached or removable lens) disposed within the frame, and a lens cleaning system coupled to (e.g., integrally formed with) the frame. The lens cleaning system includes a roll-off system. The roll-off system includes film that is pulled, stretched, laid or otherwise applied across the lens of the eyewear, from one canister to another. The film may be made of transparent material, such as plastic. The material may be fully transparent, semi-transparent, tinted, or patterned or polarized in a manner that the film does not obstruct the wearer's view The film may have a thickness and/or opacity that allows the wearer of the eyewear to see through the lens over which the film is positioned.

Roll-off systems may be mounted directly to the lens of eyewear or may be detachable from the frame as outriggers. In certain embodiments, the roll-off system consistent with implementations of the current subject matter may be integrally formed with (e.g., molded with, form a part of, etc.) the frame such that the roll-off system forms a portion of the frame. By way of example, the roll-off system may include a first canister integrally formed with a first lateral end of the frame and a second canister integrally formed with a second lateral end of the frame. Such configuration may help improve the ability of the roll-off system to clean and/or otherwise maintain a clean lens of the eyewear. The roll-off system described herein may also more quickly clean the lens of the eyewear, and improve the efficiency of the cleaning process. The roll-off system described herein may also simplify the process for the wearer to clean the lens of the eyewear. In some implementations, the roll-off system described herein may also simplify assembly and/or manufacturing of the eyewear. In some implementations, the roll-off system described herein may additionally or alternatively improve reliability of the eyewear, due at least in part to less assembled components, a more rigid frame, and/or the like. In some implementations, the roll-off system described herein may additionally or alternatively provide an improved and/or larger field of view for the wearer. In some implementations, the roll-off system described herein may additionally or alternatively provide a more lightweight eyewear. For example, less components may be needed to assembly and/or manufacture the eyewear. As noted above, the roll-off system may provide improved rigidity, so less components may be necessary to assemble and/or manufacture the eyewear, thereby reducing the weight of the eyewear and providing an improved experience for the user. The roll-off system described herein may also reduce cost of the eyewear.

FIGS. 1 through 5 illustrate an example of the eyewear, which is shown as goggle 10. The goggle 10 includes a frame having a frame body, shown as frame 20, a lens, shown as lens 50, a cushion member, shown as compressible member 60, an extender, shown as bridge 80, and a lens cleaning system, shown as roll-off system 100. In some embodiments, the roll-off system 100 is integrally formed (e.g., molded with, forms a part of, etc.) to the frame 20 and may facilitate selectively cleaning the lens 50 (e.g., removing debris from the lens 50 to provide an unobstructed view for the wearer, etc.) in a relatively simple manner (e.g., easily, quickly, etc.). For example, the roll-off system 100 may form a part of the frame 20. In some implementations, the roll-off system 100 is embedded within the frame 20. In other embodiments, the roll-off system is adhesively and/or mechanically secured to the frame 20. In some embodiments, the roll-off system 100 may be attachable or detachable from the frame 20 in a pressure-fit or snap-fit manner.

The goggle 10 provides protection to the eyes and adjacent area of the face of a wearer. For example, the lens 50 and/or the frame 20 may intercept light, wind, rain, snow, water, particulate matter (e.g., dust, dirt, mud, etc.), and the like, to protect the eyes and/or various portions of the face of a wearer of the goggle 10. As shown in FIGS. 1 through 5, the frame 20 has a first lateral end, shown as first end 22, an opposing second lateral end, shown as second end 24, a first or front side, shown as exterior side 26, and an opposing second or rear side, shown as interior side 28.

The frame 20 may be shaped to correspond with anatomical features of a wearer's face (e.g., cheeks, nose, forehead, etc.) to facilitate a proper fit of the goggle 10 when worn. As shown in FIGS. 2 through 5, the compressible member 60 is coupled to the interior side 28 of the frame 20 by the bridge 80. For example, bridge 80 may space the compressible member 60 from the interior side 28 of the frame 20. In other embodiments, the goggle 10 does not include the bridge 80 (e.g., the compressible member 60 is directly coupled to the interior side 28 of the frame 20, etc.). The compressible member 60 may thereby be positioned along the interior side 28 of the frame 20 such that the compressible member 60 is in contact with a wearer's face when the goggle 10 is worn. The bridge 80 and/or the compressible member 60 may include an impact attenuating material and/or cushion material (e.g., expanded polyurethane (EPU) foam, expanded polypropylene (EPP) foam, expanded polyethylene (EPE) foam, polyolefin foam, rubber, a flexible polymer material, etc.) to facilitate a snug and comfortable fit of the goggle 10 onto a wearer's face and/or to mitigate impact forces encountered by the goggle 10 (e.g., from flying debris, etc.).

Figure 2:
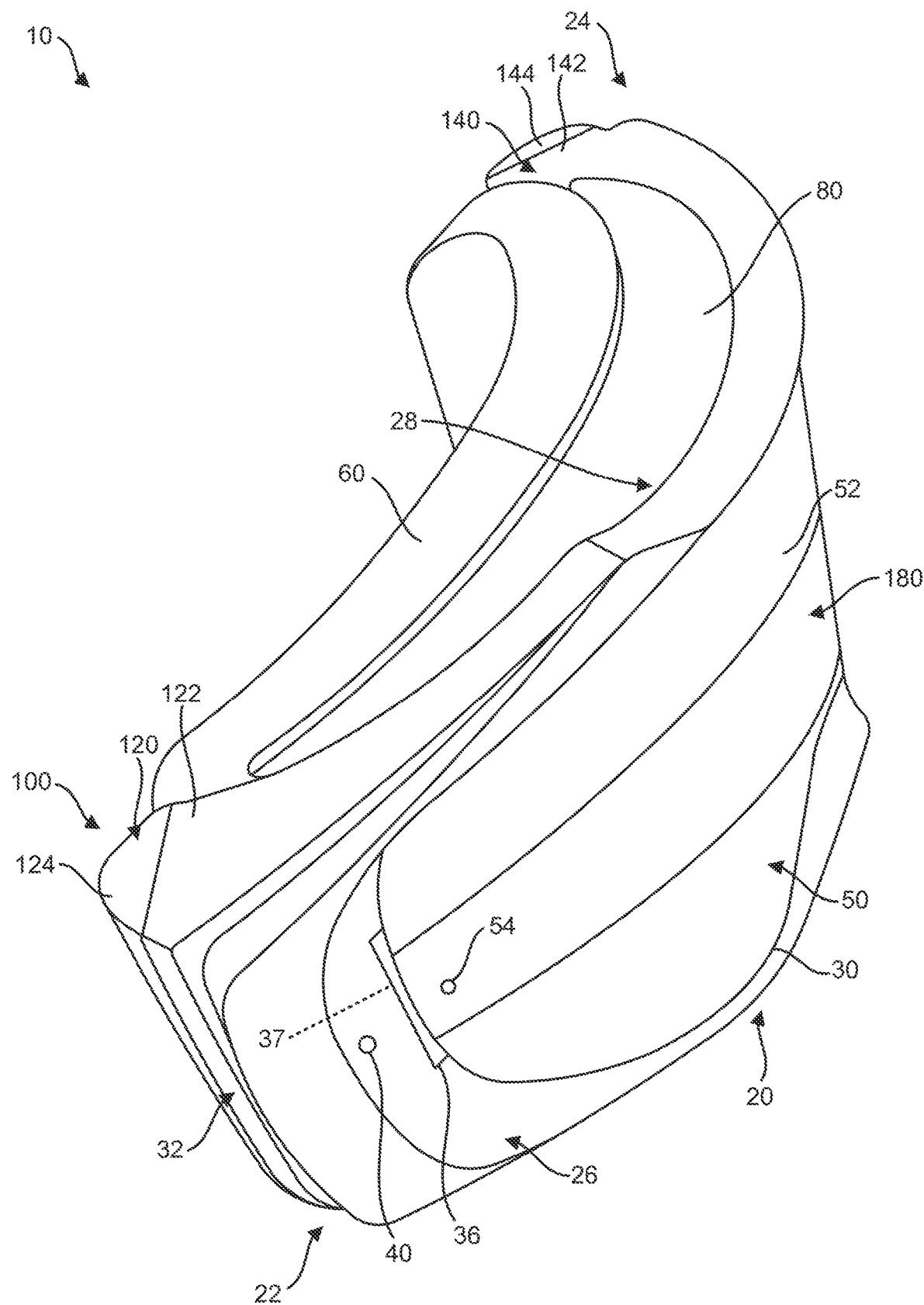
FIG. 2 is a top perspective view of the eyewear of FIG. 1, according to an example embodiment.
Figure 3:
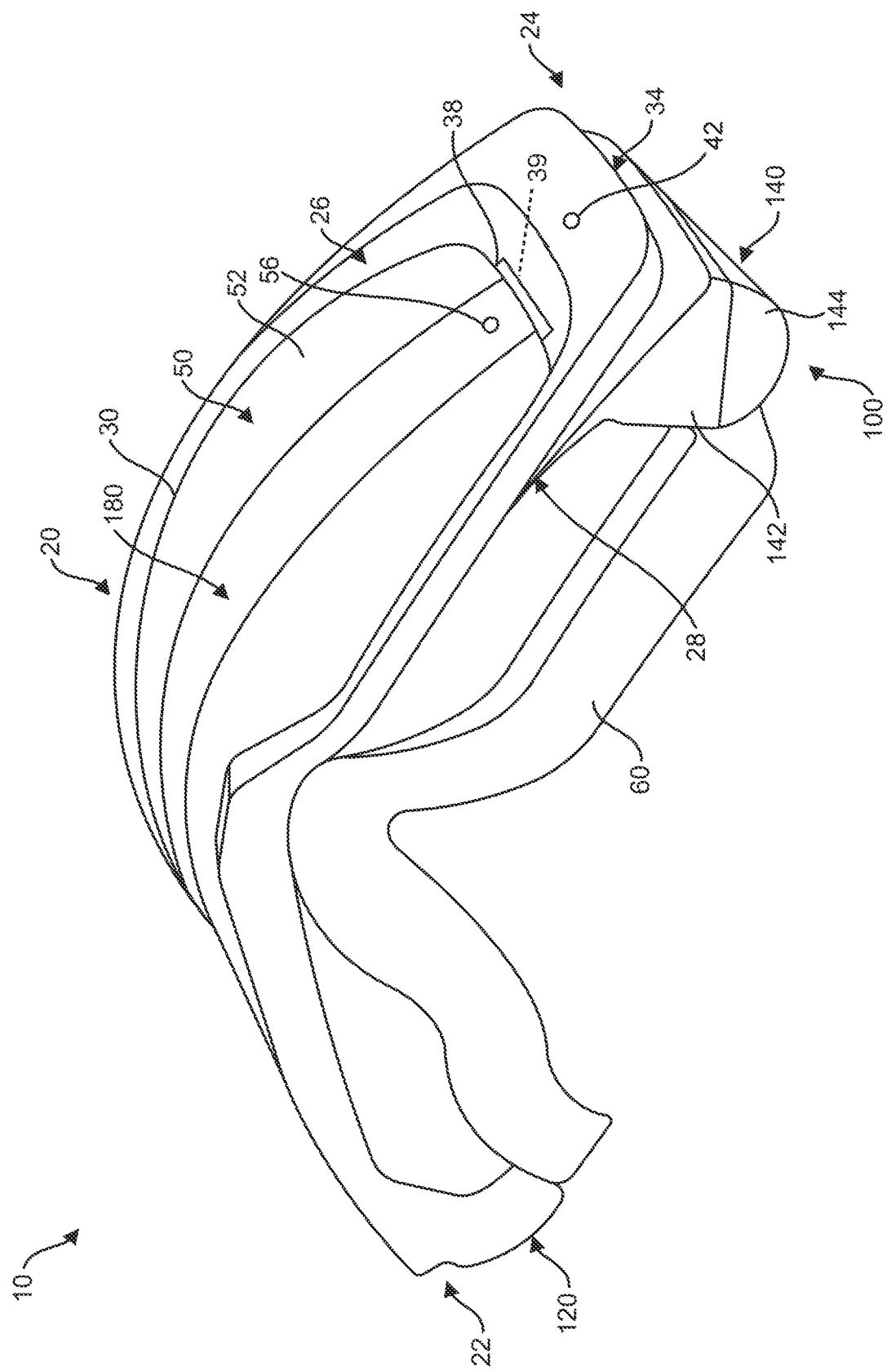
FIG. 3 is a bottom perspective view of the eyewear of FIG. 1, according to an example embodiment.

As shown in FIGS. 1 through 3, the frame 20 defines a cavity or opening, shown as lens cavity 30. The lens cavity 30 may receive the lens 50 such that the lens 50 is disposed across and/or within, and supported by the frame 20.

As shown in FIGS. 1 through 3, in one or more embodiments, the lens 50 includes a unitary, arcuate lens that extends across the entirety of the lens cavity 30 of the frame 20 (e.g., over both the left and right eyes of the wearer, from the first end 22 to the second end 24, etc.). In some embodiments, the lens 50 includes dual lenses-one positioned over each of the left and right eyes of the wearer. In some embodiments, the lens 50 is clear (e.g., substantially transparent, etc.). In other embodiments, the lens 50 includes a tinted and/or polarized coating to shade a wearer's eyes from sunlight, reduce glare, improve contrast, and/or enhance depth perception. The tinted and/or polarized coating may be various colors (e.g., black, yellow, blue, green, brown, gray, red, etc.). In some embodiments, the lens 50 includes a reflective coating (e.g., to prevent others from seeing where the wearer is looking, etc.). In some embodiments, the lens 50 is a prescription lens configured to enhance the vision of a wearer of the goggle 10. In some embodiments, the lens 50 is or includes a toroidal lens and/or a spherical lens (e.g., to prevent distortion in the vision of the wearer, etc.). In some embodiments, the lens 50 is or includes a cylindrical lens. In other embodiments, the lens 50 is still otherwise shaped.

As shown in FIGS. 2-5, in certain embodiments, the first end 22 of the frame 20 defines a first interface (e.g., a slot, an aperture, a recess, a receiver, etc.), shown as first band interface 32, and the second end 24 of the frame 20 defines a second interface (e.g., a slot, an aperture, a recess, a receiver, etc.), shown as second band interface 34. The first band interface 32 and the second band interface 34 facilitate releasably coupling a head band to the frame 20 of the goggle 10. For example, the head band may include a first band end and a second band end. The first band end may have a first coupler (e.g., a connector, a clip, etc.) that is received by the first band interface 32 to releasably secure the first band end of the head band to the first end 22 of the frame 20. The second end may have a second coupler (e.g., a connector, a clip, etc.) that is received by the second band interface 34 to releasably secure the second end of the head band to the second end 24 of the frame 20. In other embodiments, the head band is fixed to the frame 20. In some embodiments, the head band includes an elastic band and/or has a length adjuster element configured to facilitate selectively adjusting (e.g., extending, shortening, etc.) the size of the head band. The head band may thereby allow the goggle 10 to fit various sized heads.

In some embodiments, the goggle 10 includes a rip-off system. The rip-off system may facilitate detachably coupling one or more rip-off film sheets across the lens 50 (e.g., from a front of the lens 50) and the quick removal thereof. In some implementations, the tip-off system facilitates detachably coupling one or more rip-off film sheets across the lens 50 and the quick removal thereof, while the roll-off system may include a roll of film that may then be dispensed (e.g., automatically and/or via manual actuation), from one integral canister to another. The eyewear described herein may include the rip-off system and/or the roll-off system.

As shown in FIGS. 1-3, the first end 22 of the frame 20 defines a first interface, shown as first rip-off interface 40, on the exterior side 26 of the frame 20 and the second end 24 of the frame 20 defines a second interface, shown as second rip-off interface 42 on the exterior side 26 of the frame 20. In some embodiments, the first rip-off interface 40 and/or the second rip-off interface 42 include an extension (e.g., a post, a tab, a protrusion, a clip, etc.). The extension may help facilitate removal of the film sheets from the lens 50.

In some implementations, the rip-off system does not include an extension. For example, in some implementations, the rip-off system does not include a post, a tab, a protrusion, and/or a clip. In some implementations, the film sheets do not attach to the extension. In some embodiments, the first rip-off interface 40 and/or the second rip-off interface 42 define an aperture that releasably receives the extension. As shown in FIGS. 1 through 3, the lens 50 defines a first interface, shown as first rip-off interface 54, and a second interface, shown as second rip-off interface 56. According to an example embodiment, the first rip-off interface 54 and/or the second rip-off interface 56 define an aperture that releasably receives an extension (e.g., a post, a tab, a protrusion, a clip, etc.). According to an example embodiment, the first rip-off interface 40, the second rip-off interface 42, the first rip-off interface 54, and/or the second rip-off interface 56 facilitate detachably coupling one or more rip-off film sheets across the lens 50 and the quick removal thereof (e.g., when the rip-off film sheet becomes dirty obscuring the line of sight of the wearer, etc.).

As shown in FIGS. 1 through 5, the roll-off system 100 includes a first canister, shown as intake canister 120, a second canister, shown as supply canister 140, an actuator mechanism, shown as actuation system 160, and a film, shown as film 180. The intake canister 120 and the supply canister 140 may at least partially be integrally formed (e.g., molded, permanently fixed, non-detachable, etc.) with the frame 20. For example, the intake canister 120 and the supply canister 140 may form a part of and/or be embedded within the frame 20. In some implementations, the intake canister 120 and/or the supply canister 140 each define a cavity formed in the frame 20, in which the film 180 may be located. The cavities (e.g., the intake canister 120 and/or the supply canister 140 may be accessed such that the film 180 is deposited into at least one of the intake canister 120 and the supply canister 140. Thus, the film 180 may be stored and/or otherwise secured within at least one of the intake canister 120 and/or the supply canister 140. In some implementations, the intake canister 120 and/or the supply canister 140 forms a compartment portion that forms a part of at least one side of the frame 20. In alternative embodiments, the intake canister 120 and/or the supply canister 140 are adhesively secured or otherwise mechanically fastened to the frame 20.

Figure 4:
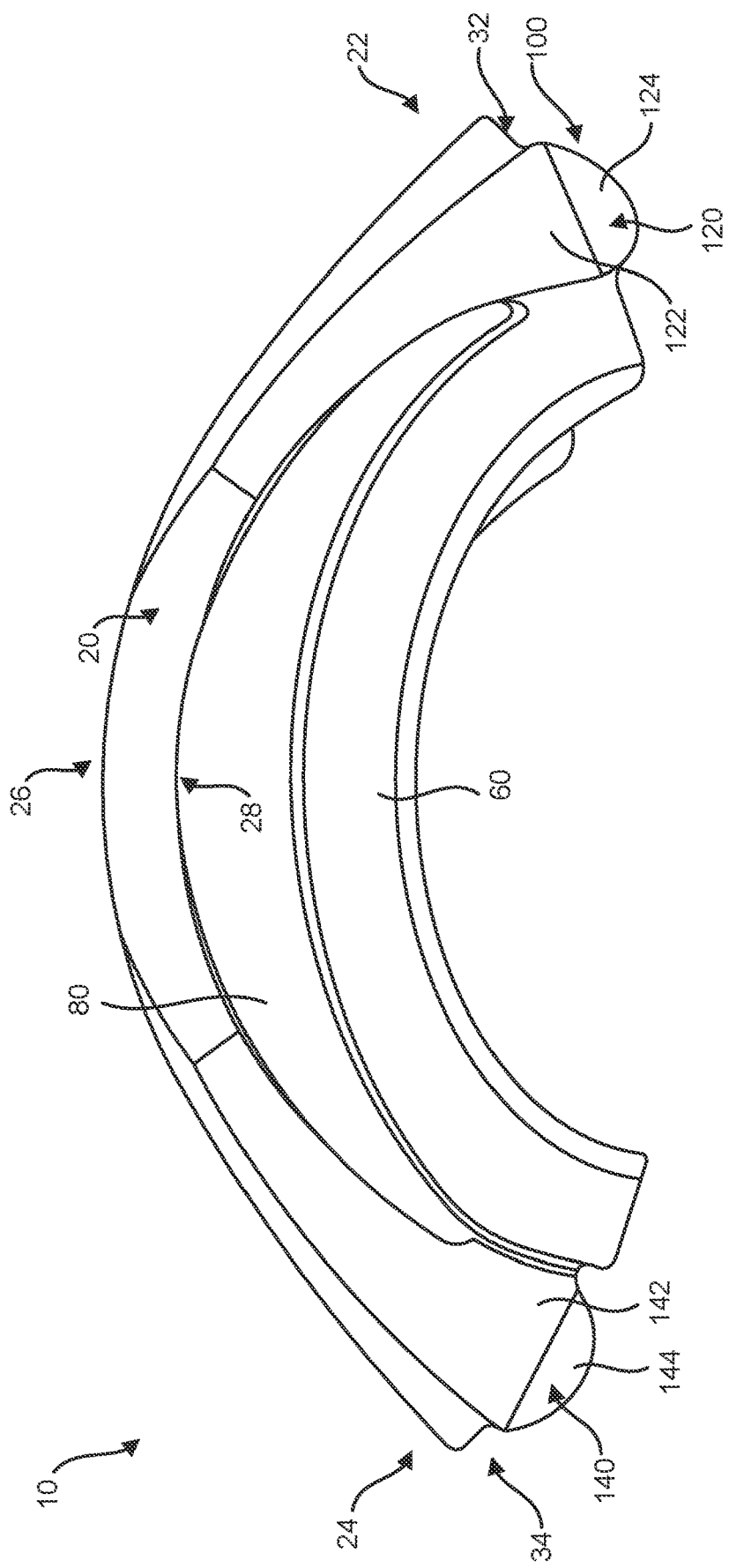
FIG. 4 is a top view of the eyewear of FIG. 1, according to an example embodiment.
Figure 5:
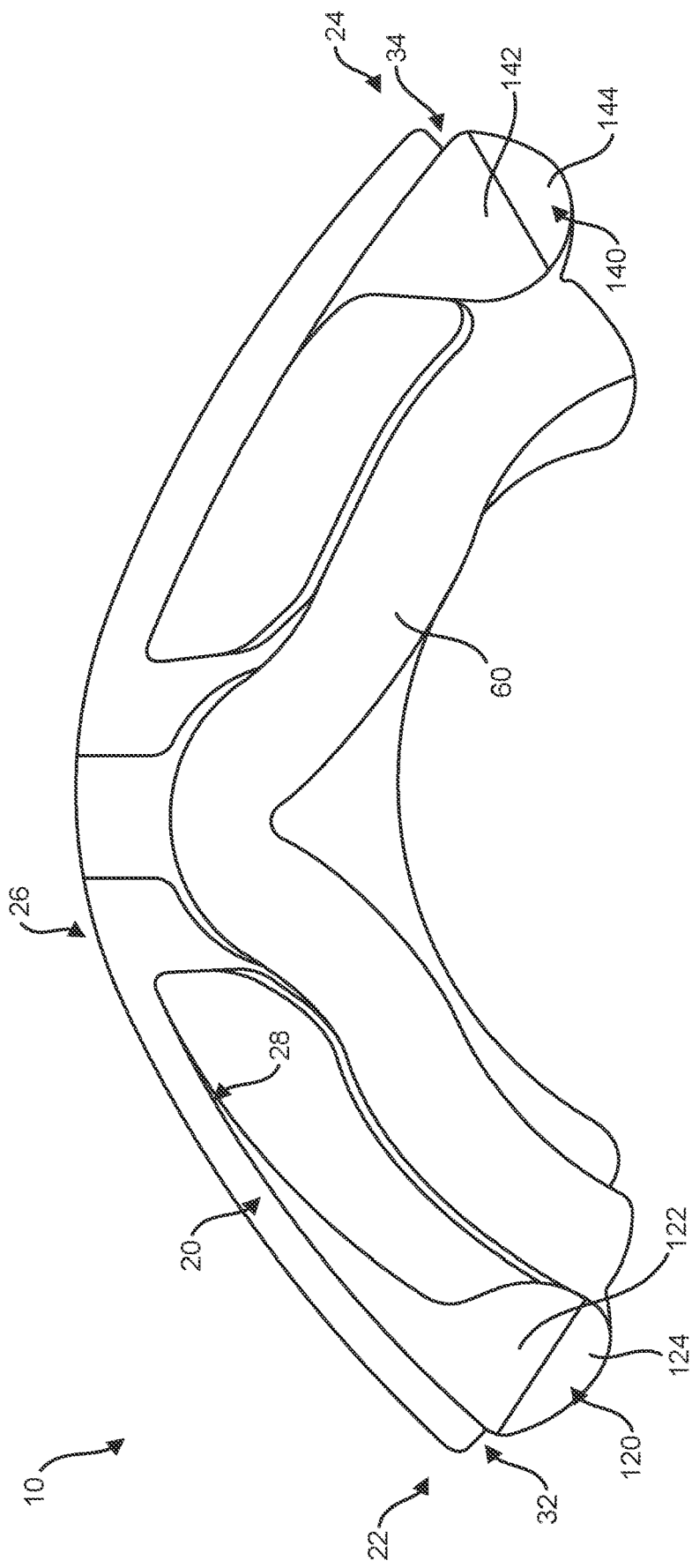
FIG. 5 is a bottom view of the eyewear of FIG. 1, according to an example embodiment.

As shown in FIGS. 2, 4, and 5, the intake canister 120 includes a first portion or base, shown as intake housing 122, and a second portion or cover, shown as intake cap 124. The intake housing 122 may be integrally formed with the first end 22 of the frame 20. The intake cap 124 may be detachably coupled to the intake housing 122.

In some embodiments, the intake housing 122 of the intake canister 120 is integrally formed with the second end 24 of the frame 20. In some embodiments, the intake cap 124 is detachable from the intake housing 122 to facilitate selectively accessing and enclosing a first interior cavity of the intake canister 120.

As shown in FIGS. 2 through 5, the intake canister 120 is coupled to and extends from the interior side 28 of the frame 20 such that the intake canister 120 is positioned behind the frame 20 (e.g., behind the first band interface 32, not substantially visible when viewing the goggle 10 from the exterior side 26, such that the intake canister 120 is not within the line of sight of a wearer of the goggle 10, etc.). In other embodiments, the intake canister 120 is coupled to and extends from the exterior side 26 of the frame 20 such that the intake canister 120 is positioned in front of the frame 20. In these embodiments, the intake canister 120 may be integrally formed with or otherwise be integrated into or with the frame 20.

As shown in FIGS. 2 through 5, the supply canister 140 includes a first portion or base, shown as supply housing 142, and a second portion or cover, shown as supply cap 144. The supply housing 142 may be integrally formed with second end 24 of the frame 20. The supply cap 144 may be detachably coupled to the supply housing 142. In other embodiments, the supply housing 142 of the supply canister 140 is integrally formed with the first end 22 of the frame 20.

In some embodiments, the supply cap 144 is detachable from the supply housing 142 to facilitate selectively accessing and enclosing a second interior cavity of the supply canister 140. As shown in FIGS. 2 through 5, the supply canister 140 is coupled to and extends from the interior side 28 of the frame 20 such that the supply canister 140 is positioned behind the frame 20 (e.g., behind the second band interface 34, not substantially visible when viewing the goggle 10 from the exterior side 26, such that the supply canister 140 is not within the line of sight of a wearer of the goggle 10, etc.). In other embodiments, the supply canister 140 is coupled to and extends from the exterior side 26 of the frame 20 such that the supply canister 140 is positioned in front of the frame 20. In these embodiments, the supply canister 140 may be integrally formed with or otherwise integrated into or with the frame 20.

As described herein, the intake canister 120 and/or the supply canister 140 of the roll-off system 100 may be integrally formed with or otherwise integrated into or with the frame 20. Integrating the intake canister 120 and/or the supply canister 140 with the frame 20 of the goggle 10 helps to ease cleaning of the eyewear for the wearer. For example, the integrated components do not need to be first coupled to the eyewear by the wearer. Instead, the wearer may simply supply the film 180 (or a roll of film) to the roll-off system (e.g., to the supply canister 140). The film 180 may then be dispensed (e.g., automatically and/or via manual actuation), from the supply canister 140, across the lens 50, to the intake canister 120. Integrating the intake canister 120 and/or the supply canister 140 with the frame 20 may also help to reduce the number of components the wearer needs to carry while using the eyewear, as the intake canister 120 and/or the supply canister 140 may not be separately attachable to the frame 20, and may be preloaded with the film 180. Thus, the wearer may only carry the eyewear in use, without needing to use any separate component or cleaning mechanism to clean the eyewear.

Referring to FIGS. 1 and 2, the first end 22 of the frame 20 defines an opening, shown as first slot 36, positioned adjacent the lens cavity 30. The first slot 36 may define a first channel 37 that extends from the exterior side 26 of the frame 20 through the frame 20 into the first interior cavity of the intake canister 120. In some implementations, the intake canister 120 is defined by an interior cavity formed in at least one side of the frame 20, such as the first side. As shown in FIGS. 1 and 3, the second end 24 of the frame 20 defines an opening, shown as second slot 38, positioned adjacent the lens cavity 30. The second slot 38 defines a second channel 39 that extends from the exterior side 26 of the frame 20 through the frame 20 into the second interior cavity of the supply canister 140. In some implementations, the supply canister 140 is defined by an interior cavity formed in at least one side of the frame 20, such as the second side.

The second interior cavity of the supply canister 140 may store a roll of the film 180 and the first interior cavity of the intake canister 120 may receive a strip of the film 180 from the roll of the film 180 stored within the supply canister 140. The actuation system 160 may facilitate selectively dispensing the strip of the film 180 from the roll of the film 180 from within the second interior cavity of the supply canister 140, across a surface, shown as front surface 52, of the lens 50, to the first interior cavity of the intake canister 120.

As shown in FIG. 1, the actuation system 160 is positioned to couple to the intake canister 120. The actuation system 160 includes a housing, shown as actuator housing 162, a pull-cord, shown as pull-string 164, and a knob, shown as pull-knob 166. The actuator housing 162 may include a rotational member (e.g., a torsional spring, etc.) that facilitates unwinding (e.g., in response to a wearer pulling on the pull-knob 166, automatically, etc.) and winding the pull-string 164 (e.g., in response to the wearer releasing the pull-knob 166 after being pulled, automatically, etc.). The actuation system 160 may dispense a new strip portion of the film 180 (e.g., a clean portion, an unused portion, etc.) from the roll of the film 180 stored in second cavity of the supply canister 140. The new strip portion of the film 180 may be dispensed through the second slot 38 in the second end 24 of the frame 20, and extend across the front surface 52 of the lens 50. The new strip portion of the film may also extend through the first slot 36 of the first end of the frame 20, and into the first interior cavity of the intake canister 120, for example, in response to a wearer of the goggle 10 pulling on the pull-knob 166. The intake canister 120 is thereby configured to receive and store the old strip portion of the film 180 (e.g., the used portion, the dirty portion, roll up the film strip onto a spindle, etc.). In some embodiments, the frame 20 defines an extension or scraper element positioned to engage the strip of the film 180 as the film 180 is fed into the first slot 36. When the strip of film is fed into the first slot 36, the extension or scraper element may remove particles (e.g., debris, mud, dirt, particles, etc.) from the film 180 as the film 180 enters the intake canister 120. In some embodiments, the roll-off system 100 is a continuous roll-off system including a single, continuous loop of film similar to that disclosed in U.S. patent application Ser. No. 15/182,018, filed on Jun. 14, 2016, which is incorporated herein by reference in its entirety.

In some embodiments, the goggle 10 (e.g., the frame 20) additionally and/or alternatively includes one or more wipers 190. The one or more wipers may be positioned at various locations along the frame 20, such as along first and/or second lateral sides of the frame 20. In some implementations, the one or more wipers may be positioned at various locations along the lens 50, such as along first and/or second lateral sides of the lens 50. In some implementations, the one or more wipers are stationary, such as relative to the frame 20 and/or the lens 50. In such implementations, the one or more wipers may clean debris or other substances from the film 180 and/or lens 50, such as when the film is rolled, pulled, and/or otherwise moved across the lens 50. In other implementations, the one or more wipers may pivot, rotate, or may otherwise move across at least a portion of the front surface 52 of the lens 50 to clean debris or other substances from the front surface 52 of the lens 50 and/or from the film 180. In some embodiments, the one or more wipers (e.g., automatically or via manual actuation) move across the front surface 52 before the film 180 is applied to the lens 50. The one or more wipers may further improve the cleaning of the eyewear (e.g., via increased speed, performance, and efficiency).

It is important to note that the construction and arrangement of the elements of the systems, methods, and/or apparatuses as shown in the example embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the goggle may be constructed from any of a wide variety of materials that provide sufficient strength or durability, in any of a wide variety of colors, textures, and combinations.

Embodiments have been described in connection with the accompanying drawings. However, it should be understood that the figures are not drawn to scale. Distances, angles, shapes, etc. are merely illustrative and do not necessarily bear an exact relationship to actual dimensions and layout of the articles that are illustrated. In addition, the foregoing embodiments have been described at a level of detail to allow one of ordinary skill in the art to make and use the articles, parts, different materials, etc. described herein. A wide variety of variation is possible. Articles, materials, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or configurations are in any way required for one or more embodiments. The terms "comprising," "including," "having," and the like are synonymous and are used inclusively, in an open-ended fashion, and do not exclude additional elements, features, acts, operations, and so forth. The term "consisting essentially of" can be used anywhere where the terms comprising, including, containing or having are used herein, but consistent essentially of is intended to mean that the claim scope covers or is limited to the specified materials or steps recited and those that do not materially affect the basic and novel characteristic(s) of the claimed invention. Also, the term "consisting of" can be used anywhere where the terms comprising, including, containing or having are used herein, but consistent of excludes any element, step, or ingredient not specified in a given claim where it is used.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

Additionally, in the subject description, the word "example" is used to mean serving as an example, instance, or illustration. Any embodiment or design described herein as "example" is not necessarily to be construed as preferred or advantageous over other embodiments or designs. Rather, use of the word example is intended to present concepts in a concrete manner. Accordingly, all such modifications are intended to be included within the scope of the present inventions. Other substitutions, modifications, changes, and omissions may be made in the design, operating conditions, and arrangement of the preferred and other example embodiments without departing from scope of the present disclosure or from the spirit of the appended claims.

The invention claimed is:

1. An eyewear, comprising:
   a frame having a first lateral end and an opposing second lateral end, the frame defining a lens cavity, the first lateral end having a first slot therethrough and positioned laterally adjacent to the lens cavity, and the second lateral end having a second slot therethrough and positioned laterally adjacent to the lens cavity;
   a lens disposed within the lens cavity of the frame; and
   a roll-off system including:
      a first canister at least partially integral with the first lateral end of the frame and in communication with the first slot, the first canister defining a first interior cavity configured to store a roll of film with a first portion of the film extending from the first interior cavity, through the first slot, and to the lens; and
      a second canister at least partially integral with the opposing second lateral end of the frame and in communication with the second slot, the second canister defining a second interior cavity configured to receive a second portion of the film from the roll of film with the second portion of the film extending from the lens, through the second slot and into the second interior cavity; and
   a first rip-off interface at the first lateral end of the lens/frame disposed between the first canister and the first slot and a second rip-off interface at the second lateral end of the lens/frame disposed between the second canister and the second slot, wherein the first rip-off interface and the second rip-off interface are configured to facilitate detachably coupling a rip-off film sheet across the lens.

2. The eyewear of claim 1, wherein the first rip-off interface and the second rip-off interface each define an aperture, each aperture being configured to detachably receive a respective extension.

3. The eyewear of claim 1, wherein the first canister comprises a first housing at least partially integral with the first lateral end of the frame and the second canister comprises a second housing at least partially integral with the second lateral end of the frame.

4. The eyewear of claim 3, wherein the first canister and the second canister extend from a rear side of the frame.

5. The eyewear of claim 3, wherein the first canister includes a first cap detachably coupled to the first housing to facilitate selectively accessing and enclosing the first interior cavity of the first canister.

6. The eyewear of claim 3, wherein the second canister includes a second cap detachably coupled to the second housing to facilitate selectively accessing and enclosing the second interior cavity of the second canister.

7. The eyewear of claim 1 further comprising an actuator mechanism configured to facilitate selectively dispensing an unused portion of the roll of film from the first canister, through the first slot, across the lens, through the second slot, and into the second canister.

8. The eyewear of claim 7, wherein the actuator mechanism includes a pull-cord configured to facilitate manually dispensing the unused portion of the roll of film between the first canister and the second canister.

9. The eyewear of claim 1, wherein the lens is removable.

10. The eyewear of claim 1 wherein the first lateral end of the frame has a first band interface configured to releasably connect a first end of a head band to the frame, and the second lateral end of the frame has a second band interface configured to releasably connect a second end of the head band to the frame.

11. The eyewear of claim 1 further comprising one or more wipers configured to clean debris or other substances from the film.

12. An eyewear, comprising:
   a frame having a first lateral end and an opposing second lateral end, the frame defining a lens cavity, the first lateral end having a first slot therethrough and positioned laterally adjacent to the lens cavity, and the second lateral end having a second slot therethrough and positioned laterally adjacent to the lens cavity;
   a lens disposed within the lens cavity of the frame; and
   a roll-off system including:
      a first canister in communication with the first slot, the first canister defining a first interior cavity configured to store a roll of film with a first portion of the film extending from the first interior cavity, through the first slot, and to the lens;
      a second canister in communication with the second slot, the second canister defining a second interior cavity configured to receive a second portion of the film from the roll of film with the second portion of the film extending from the lens, through the second slot and into the second interior cavity; and
      a first rip-off interface comprising an extension disposed on the first lateral end of the frame and inboard of the first canister and a second rip-off interface comprising an extension disposed on the second lateral end of the frame and inboard of the second canister, wherein the first rip-off interface and the second rip-off interface are configured to facilitate detachably coupling a rip-off film sheet across the lens.

13. The eyewear of claim 12, wherein the first rip-off interface and the second rip-off interface each define an aperture, each aperture being configured to detachably receive the respective extension.

14. The eyewear of claim 12, wherein the first canister is at least partially integral with the first lateral end of the frame and the second canister is at least partially integral with the second lateral end of the frame and wherein at least one of the first canister and the second canister extend from a rear side of the frame.

15. The eyewear of claim 14, wherein the first canister comprises a first housing and a first cap detachably coupled to the first housing to facilitate selectively accessing and enclosing the first interior cavity of the first canister.

16. The eyewear of claim 14, wherein the second canister comprises a second housing and a second cap detachably coupled to the second housing to facilitate selectively accessing and enclosing the second interior cavity of the second canister.

17. The eyewear of claim 12 further comprising an actuator mechanism configured to facilitate selectively dispensing an unused portion of the roll of film from the first canister, through the first slot, across the lens, through the second slot, and into the second canister.

18. The eyewear of claim 17, wherein the actuator mechanism includes a pull-cord configured to facilitate manually dispensing the unused portion of the roll of film between the first canister and the second canister.

19. The eyewear of claim 12 wherein the first lateral end of the frame has a first band interface configured to releasably connect a first end of a head band to the frame, and the second lateral end of the frame has a second band interface configured to releasably connect a second end of the head band to the frame.

20. The eyewear of claim 12, wherein a first lateral end of the lens defines the first rip-off interface and an opposing second lateral end of the lens defines the second rip-off interface.

21. An eyewear, comprising:
a frame having a first lateral end and an opposing second lateral end, the frame defining a lens cavity, the first lateral end having a first slot therethrough and positioned laterally adjacent to the lens cavity, and the second lateral end having a second slot therethrough and positioned laterally adjacent to the lens cavity;
a lens disposed within the lens cavity of the frame; and
a roll-off system including:
a first canister at least partially integral with the first lateral end of the frame and extending from a rear side of the frame, the first canister defining a first interior cavity in communication with the first slot and configured to store a roll of film with a first portion of the film extending from the first interior cavity, through the first slot, and to the lens; and
a second canister at least partially integral with the opposing second lateral end of the frame and extending from a rear side of the frame in communication with the second slot, the second canister defining a second interior cavity in communication with the second slot and configured to receive a second portion of the film from the roll of film with the second portion of the film extending from the lens, through the second slot and into the second interior cavity.

22. The eyewear of claim 21, comprising a first cap detachably coupled to the first canister to facilitate selectively accessing and enclosing the first interior cavity of the first canister.

23. The eyewear of claim 21, comprising a second cap detachably coupled to the second canister to facilitate selectively accessing and enclosing the second interior cavity of the second canister.

24. The eyewear of claim 21 further comprising an actuator mechanism configured to facilitate selectively dispensing an unused portion of the roll of film from the first canister, through the first slot, across the lens, through the second slot, and into the second canister.

25. The eyewear of claim 24, wherein the actuator mechanism includes a pull-cord configured to facilitate manually dispensing the unused portion of the roll of film between the first canister and the second canister.

26. The eyewear of claim 21, wherein the lens is removable.

27. The eyewear of claim 21 wherein the first lateral end of the frame has a first band interface configured to releasably connect a first end of a head band to the frame, and the second lateral end of the frame has a second band interface configured to releasably connect a second end of the head band to the frame.

28. The eyewear of claim 21 further comprising one or more wipers configured to clean debris or other substances from the film.

29. An eyewear, comprising:
a frame having a first lateral end and an opposing second lateral end, the frame defining a lens cavity, the first lateral end having a first slot therethrough and positioned laterally adjacent to the lens cavity, and the second lateral end having a second slot therethrough and positioned laterally adjacent to the lens cavity;
a lens disposed within the lens cavity of the frame; and
a roll-off system comprising
a first canister at least partially integral with the first lateral end of the frame and extending from a rear side of the frame, the first canister comprising
a first interior cavity in communication with the first slot and configured to store a roll of film with a first portion of the film extending from the first interior cavity, through the first slot, and to the lens; and a first cap detachably coupled to the first canister to facilitate selectively accessing and enclosing the first interior cavity of the first canister; and
a second canister at least partially integral with the opposing second lateral end of the frame and extending from a rear side of the frame, the second canister comprising
a second interior cavity in communication with the second slot and configured to receive a second portion of the film from the roll of film with the second portion of the film extending from the lens, through the second slot and into the second interior cavity; and a second cap detachably coupled to the second canister to facilitate selectively accessing and enclosing the second interior cavity of the second canister; and
an actuator mechanism configured to facilitate selectively dispensing an unused portion of the roll of film from the first canister, through the first slot, across the lens, through the second slot, and into the second canister.

30. The eyewear of claim 29, wherein the actuator mechanism includes a pull-cord configured to facilitate manually dispensing the unused portion of the roll of film between the first canister and the second canister.

31. The eyewear of claim 29 wherein the first lateral end of the frame has a first band interface configured to releasably connect a first end of a head band to the frame, and the second lateral end of the frame has a second band interface configured to releasably connect a second end of the head band to the frame.

32. The eyewear of claim 29, wherein the lens is removable.

* * * * *